US009291579B2

(12) United States Patent
Hu et al.

(10) Patent No.: US 9,291,579 B2
(45) Date of Patent: Mar. 22, 2016

(54) METHOD OF ESTIMATING CHORDAL HOLDUP VALUES OF GAS, OIL AND WATER FOR TOMOGRAPHIC IMAGING OF A THREE-PHASE FLOW THROUGH A VOLUME

(75) Inventors: Bin Hu, Kjeller (NO); Christopher John Lawrence, Kjeller (NO)

(73) Assignee: Institute of Energy Technology, Kjeller (NO)

(*) Notice: Subject to any disclaimer, the term of this patent is extended or adjusted under 35 U.S.C. 154(b) by 282 days.

(21) Appl. No.: 14/111,772

(22) PCT Filed: Apr. 16, 2012

(86) PCT No.: PCT/NO2012/050067
§ 371 (c)(1),
(2), (4) Date: Jun. 25, 2014

(87) PCT Pub. No.: WO2012/141600
PCT Pub. Date: Oct. 18, 2012

(65) Prior Publication Data
US 2014/0307846 A1 Oct. 16, 2014

Related U.S. Application Data

(60) Provisional application No. 61/475,917, filed on Apr. 15, 2011.

(30) Foreign Application Priority Data

Apr. 15, 2011 (NO) .................................. 20110606

(51) Int. Cl.
*G01N 23/04* (2006.01)
*G01N 23/12* (2006.01)

(52) U.S. Cl.
CPC .............. *G01N 23/046* (2013.01); *G01N 23/12* (2013.01); *G01N 2223/419* (2013.01); *G01N 2223/601* (2013.01); *G01N 2223/635* (2013.01)

(58) Field of Classification Search
CPC ...... A61B 6/482; A61B 6/032; A61B 6/4241; A61B 6/03; G01N 23/046; G01N 2223/419; G01N 2223/423; G01N 23/087; G01N 2223/616; G01N 9/24
USPC .......................................................... 378/5
See application file for complete search history.

(56) References Cited

U.S. PATENT DOCUMENTS 5,552,598 A * 9/1996 Kessler .................. E21B 47/10
250/269.3
5,854,820 A 12/1998 Slijkerman et al.
(Continued)

FOREIGN PATENT DOCUMENTS

WO 97/42493 A1 11/1997
WO 2009/093927 A1 7/2009

OTHER PUBLICATIONS

Bin Hu, et al., "A Fast X-Ray Tomography System in Multiphase Pipe Flow Measurement", date Oct. 12, 2011, pp. 1-18.
(Continued)

*Primary Examiner* — Hoon Song
(74) *Attorney, Agent, or Firm* — Sutherland Asbill & Brennan LLP

(57) ABSTRACT

A method of estimating chordal holdup values of gas, oil, and water ($\epsilon_G$, $\epsilon_O$, $\epsilon_W$) for tomographic imaging of a three-phase flow through a volume, including:
providing an X-ray source for irradiating through said volume and X-ray sensors for discriminating between a first and a second radiation bands,
conducting first calibration measurements ($I_G^S$, $I_O^S$, $I_W^S$) of said first radiation band,
conducting second calibration measurements ($I_G^H$, $I_O^H$, $I_W^H$) of said second radiation band,
arranging a mixture of two or more fluids,
irradiating said volume and conducting X-ray measurements ($I^S$, $I^H$) in said radiation bands,
establishing a relationship between a function of holdup values $f(\epsilon_G, \epsilon_W)$ of at least gas and water and said X-ray measurements ($I^S$, $I^H$),
searching holdup values ($\epsilon_G$, $\epsilon_W$) that minimize said function of holdup values $f(\epsilon_G, \epsilon_W)$ under the constraints of the sum of said holdup values is more than or equal to zero and less than or equal to one, i.e. that $0 \leq \epsilon_G + \epsilon_W \leq 1$.

15 Claims, 9 Drawing Sheets

(56) References Cited

U.S. PATENT DOCUMENTS

| | | | |
|---|---|---|---|
| 7,829,860 B2 | 11/2010 | Nygard et al. | |
| 2004/0141583 A1* | 7/2004 | Siddiqui | G01N 23/046 378/52 |
| 2013/0313437 A1* | 11/2013 | Li | G01N 23/046 250/363.03 |

OTHER PUBLICATIONS

Bin Hu, et al., Development of an X-Ray Computed Tomography (CT) System With Sparse Sources: Application to Three-Phase Pipe Flow Visualization, Experiments in Fluids; Experimental Methods and Their Applications to Fluid Flow, Springer, Berlin, DE, vol. 39, No. 4, Oct. 1, 2005, pp. 667-678.

M. Acikgoz, et al., "An Experimental Study of Three-Pahse Flow Regimes", 1991, Int. J. Multiphase Flow, vol. 18, No. 3, p. 341.

A.R. W. Hall, "Multiphase Flow of Oil-Water-Gas in Horizontal Pipes", Ph.D. dissertation, University of London, 1992.

Bin Hu, et al., "Void Distribution in the Liquid Layer in Stratified Wavy Flows Measured With an X-Ray Computed Tomography Instrument", 14th BHR Conference, Cannes, France, 2009.

Bin Hu, et al., "Entrainment of as Into Slugs and Its Subsequent Transport in Two-Phase Slug Flow", 7th North American Conference on Multiphase Technology, Banff, Canada, Jun. 2-4, 2010.

M. Langsholt, et al., "Pipe Inclination Effects on Three-Phase Slug Flow Characteristics", IFE Internal Report IFE/KF/R/2011-0064, Institute for Energy Technology, Norway, 2002.

U.A. Odozi, "Three-Phase Gas-Liquid-Liquid Slug Flow", Ph.D. thesis, University of London, 2000.

L. Pan, "High Pressure Three-PHASW (Gas/Liquid/Liquid Flow)", Ph.D. thesis Imperial College, University of London, 1996.

D. P. Sobocinski, "Horizontal Concurrent Flow of Air, Gas-Oil, and Water INA Horizontal Pipe", M.S. thesis University of Oklahoma, 1955.

A. Valle, "Three Phase Gas-Oil-Water Pipe Flow", Ph.D. thesis, University of London, 2000.

R. J. Wilkens, "Prediction of the Flow Regime Transitions in High Pressure, Large Diameter Inclinded Multiphase Pipelines", Ph.D. dissertation, Ohio University, Ohio, 1997.

U.A. Odozi, "Chapter 5 Flow Pattern and Flow Pattern Maps", Ph.D. thesis, pp. 186-290.

* cited by examiner

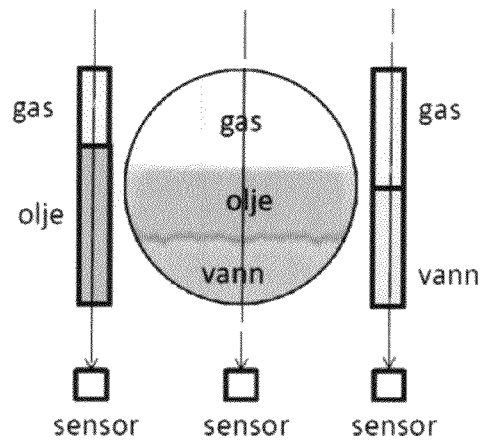
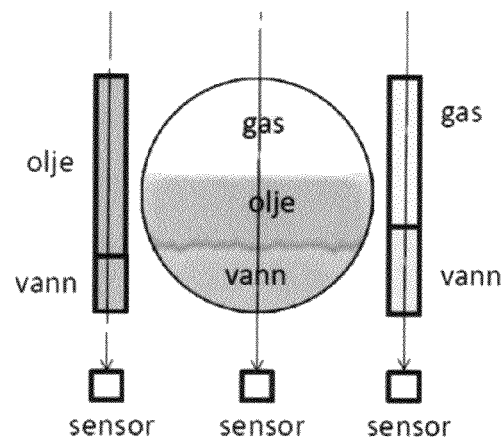
Fig. 10a           Fig. 10b
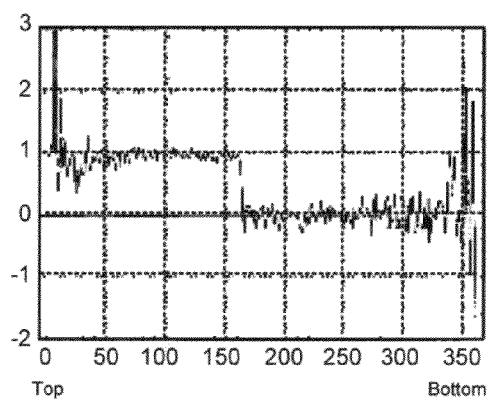
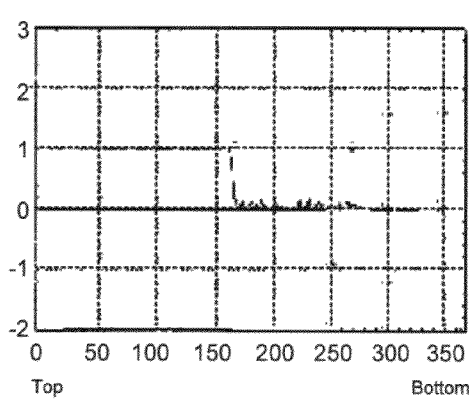
Fig. 11a           Fig. 11b

METHOD OF ESTIMATING CHORDAL HOLDUP VALUES OF GAS, OIL AND WATER FOR TOMOGRAPHIC IMAGING OF A THREE-PHASE FLOW THROUGH A VOLUME

INTRODUCTION

The present invention relates to a three-phase X-ray tomography system. The invention has been developed and tested in a large diameter multiphase pipeline flow facility (Well flow loop) at Institute for Energy Technology, Norway. The X-ray system comprises two or more channels running independently, each channel comprising an X-ray source, a detector panel with a large number of pixels, and PC controlled hardware. The detector panels are mounted perpendicular to each other and are collimated to reduce "cross talk" between the channels. To achieve a three-phase measurement, a thin copper filter is placed on the top of one section of each detector to harden the X-ray beams so as to give two different energy bands required for distinguishing oil and water. The fast response of the system enables one to record the flow at a sampling rate up to 300 frames per second, the same rate as for a two-phase system. By using the X-ray tomography system of the invention, one can obtain more valuable information on three-phase gas-oil-water flows than conventional techniques. Moreover, phase distributions in the cross-section can be measured in better detail at high temporal and spatial resolution which will be helpful to validate various flow models.

BACKGROUND ART AND PROBLEMS RELATED THERETO

Multiphase pipeline flows occur widely in the petroleum industry and in numerous chemical process plants. Of particular importance is the development of reliable models that can simulate their complex flow characteristics. A special challenge during the transport of gas condensate and oil well streams in the petroleum industry is the prediction of phase inventory and pressure loss in a long distance, large diameter multiphase pipeline at large water depths. Accurate flow models are essential to safe and cost efficient design and operation of field pipelines and topside downstream facilities.

Researches have been carried out for several decades in the past to understand the interactions of phases and flow characteristics. Different flow regimes were categorized to describe the interfacial macro- and meso-structures in two-phase gas-liquid and three-phase gas-liquid-liquid flows. Many experiments were conducted to study the flow details in each flow regime by using the state-of-art technologies, e.g. gamma densitometer, hot-film anemometer, LDA, PIV/PTV, ECT and X-ray computer tomograph. Information obtained has further strengthened our knowledge and provided insights to the local flow structures, such as turbulence, phase fraction and drop size. However, compared to the large amount of work in two-phase gas-liquid flows, few data are available for three-phase flows, and particularly for three-phase flows in large diameter pipes. Most of the few reported studies are only focused on the bulk parameters, e.g. pressure drop, mean holdups and flow regimes, based on the measurements with dual-energy gamma densitometer, quick closing valve and pressure transducers (see Sobocinski, 1955; Hall, 1992; Ackigoz et al., 1992; Pan, 1996; Wilkens, 1997; Morten et al., 2002; Odozi, 2000; Valle, 2000). Due to the lack of capable instruments, detailed information in a three-phase system on flow structure and phase distribution is even scarcer. Hu et al. (2005) reported the use of an X-ray tomograph in gas-oil-water flows in a 3 inch (76 mm) pipe, a system pioneered at imperial College London. Due to the lack of detectors with sufficient energy discrimination, the system resorts to moving filters to give alternating high and low energy exposures. Despite its successful application, the use of rotating filters led to a low time resolution, with 5 Hz as maximum sampling rate. The low temporal resolution has resulted in a loss of synchronization of structure between the horizontal and vertical measurements in fast flows, which brings difficulties in accurately reconstructing the cross-sectional tomographs.

Recently, an X-ray computer tomography system has been developed at Institute for Energy Technology which is based on the system pioneered at Imperial College but designed and manufactured with more up-to-date technologies, and which forms a basis for the present invention. The system is essentially a fast response two-phase system, giving a maximum sampling rate of 300 Hz. Latest applications of this system have shown versatile competence in measuring and visualizing complex multiphase flows (see Hu et al., 2009, 2010). Using such system, important flow behaviour of gas, oil and water phases in stratified and slug flows can be captured with a rather good accuracy.

The present invention improves the X-ray tomography measurement capability for gas-oil-water three-phase flows. In what follows, the next section illustrates the components and installation of the three-phase X-ray tomography system, followed by the description of the data analysis algorithm which may be used in the invention in the subsequent section. Then the next subsequent section shows the typical results that one can obtain using the present invention utilizing the described X-ray tomography system.

The Three-Phase X-Ray Tomography System

The X-ray tomography system comprises two or more generally identical channels, each channel comprising an X-ray source, an X-ray camera and computer controlled hardware, please see FIG. 1. The X-ray source has an anode-grounded, metal-ceramic vacuum tube with disc-shaped oil-filled insulator (model MB70-6-B-450, InnospeXion). A collimator is employed to provide a narrow X-ray beam. The two sources are arranged in fixed positions, one at the top and one horizontally relative to the enclosure, providing vertical and horizontal projections through the test pipe section, respectively, when the test pipe section is horizontally arranged. The X-ray detectors are high-resolution, high-sensitivity CdTe-CMOS linear arrays with an effective pixel area of 1500×56 pixels (150 mm×5.6 mm). The X-ray system is accompanied by a computer with a software suite which controls the data acquisition process, calibration of the detector arrays, data display, and storage of the results. The tomography system is fitted in a lead shielding box with steel sleeves on both sides for safe operation. This lead box and data collection PC's are built into a unit that is mounted on the IFE Well Flow Loop, and follows the loop as it is inclined from horizontal to vertical. In an embodiment the pipe test section is made of transparent PVC. The present embodiment of the X-ray system and its working principles are to some extent analogous to the one installed on the WASP flow rig at Imperial College London, UK, (see Hu et al., 2005). However, the present system does not use mechanical rotating sensor components, and thus can achieve the same maximum sampling frequency of 300 Hz for three-phase flows as for two-phase flows. This fast response allows for detailed studies of flows with rapidly changing structures, such as large wave and slug flows.

To achieve a three-phase measurement, one may use arrange a copper filter over a part of the camera (see FIG. 2).

The copper filter absorbs (scatters) some of the X-rays, changing the energy spectrum seen by the camera. Since the lower energy (soft) X-rays are preferentially absorbed by the copper, the spectrum is said to be "hardened". The X-ray absorption coefficients of the three working fluids oil, water and gas differ significantly in the low energy part of the spectrum. Oil and water have more similar coefficients in the high energy part of the spectrum. Thus, the high energy part of the spectrum serves to distinguish gas and liquid, while the difference between measurements in the high and low parts of the energy spectrum allows us to distinguish oil and water. Other sensor designs may discriminate between the energy levels of the incoming X-ray photons individually, and such sensors arrays may alternatively be employed.

During the design of an embodiment of the system, an optimisation process has been carried out to study the optimum filter thickness. Filters of different thicknesses in combination with the variance of the X-ray energy were tested and assessed for performance. It was found that for the current system, the optimum solution is the use of 0.1 mm thickness copper filter under the operation of the X-ray tube at 60 kV and 4 µA. FIG. 2a illustrates the schematic diagram for the use of a thin copper filter on the top of one section of Camera 1.

FIG. 2b shows a typical image produced by plotting a single frame of 150 mm length and 5.6 mm width (please notice the exaggerated width to length ratio) of the raw image visualized by Camera 1 as captured when the test section is filled with gas. To increase the total number of photons from hard beams that hit the detector, the filtered region is designed to cover ⅔ of the whole width (i.e. ~3.7 mm). After removing the noisy pixels near the filter edge, an effective width of 1.6 and 2.9 mm is used for soft and hard beams, respectively.

With the experimental sensor setup wherein ⅔ of the width of the sensor cell array is filter covered and thus measures "hard" X-rays and the adjacent ⅓ width of the sensor cell array is not, and measures "soft (and hard)" X-rays, and the length of the sensor array (here 150 mm) is transverse to the general transport direction through the pipe section, it is evident that the data measured from "hard" and "soft" beams are spatially separated by a distance, averagely about 3 mm apart in the axial direction. This places a lower bound on the resolution of the system. For other sensor cell types than the presently used, such as for a sensor by Interon, wherein the same cell can discriminate X-ray energies of individual photons into separate bins, this is not a problem. In practice with the present setup using a copper filter, the signal represents a time-average over a short time interval (typically 3-10 ms). During this time, the fluids move a distance, where u is the local velocity of the fluid, which we assume is generally axial. For most of the flows we study, the velocity is in the range of >0.5 m/s, so that the spatial separation has a smaller influence on the results.

The present three-phase X-ray tomography system is installed on the high pressure Well Flow Loop at IFE, Norway. The rig comprises a 25 m long test section of 100 mm inner diameter that can be inclined at desired inclination angles, from 0 to ±90 degrees, please see details given in Hu et al., 2010. For higher inclination angles (>5 degree) a bend can be introduced between the first 10 meters of the test section and the rest, which can be inclined up to vertical. Light oil (Exxsol D80), tap water and high density gas ($SF_6$) are used as test fluids. At the inlet to the test section the fluids enter with the phases separated by horizontal plates to reduce the influence of inlet geometry on downstream flows. At the outlet end of the test section the flow enters a pre-separator intended to generate an approximately constant liquid level and eliminate any suction effect when a slug passes into the downhill return pipe. The current X-ray tomograph system is located 2 m upstream of the pre-separator.

FIGURE CAPTIONS

The invention is illustrated in the attached drawing Figures wherein

FIG. 1 is a simplified cross section and system overview of the three-phase X-ray tomography system.

FIG. 2a is a schematic diagram of a cross section through the source/collimator which radiates through the test section pipe to the partly Cu-filter covered X-ray sensor array's cross-section, here 5.6 mm. FIG. 2b is an image captured by the sensor array of 150 mm length across the pipe and 5.6 mm width, when the pipe section is gas-filled. The unfiltered "soft" sensor region (not covered by the Cu-filter) is shown to the left, and the filtered "hard" sensor region due to the Cu-filter is shown to the right. Note the compressed length ratio.

FIGS. 3a, b, and c, respectively, show calibration diagrams for gas, oil, and water, respectively. The lower curves in each diagram show signals from "hard" sensor portions, the upper curves show signals from "soft" sensor portions.

FIGS. 6a, b, c, d, e, f, g, and h shows a sequence of tomographic images reconstructed from the passage of a three-phase slug. Green, red and blue are for gas, oil, and water as above.

Figure 7:
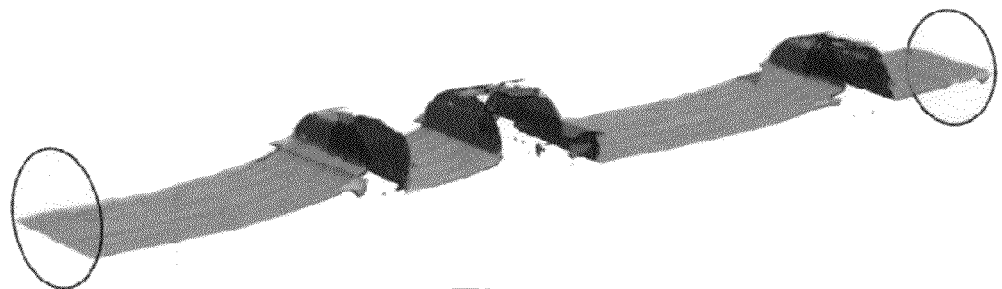

FIG. 7 is a 3-D tomographic reconstruction of a gas-liquid interface (green) from the contour plot of a gas volume fraction of 0.8.

Figure 8:
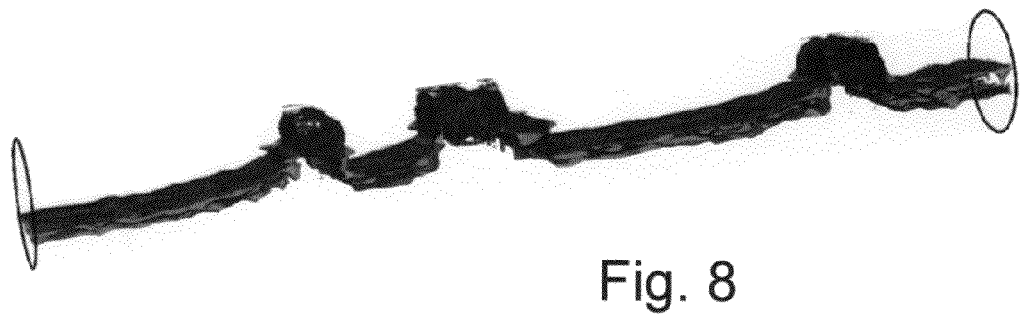

FIG. 8 is a 3-D reconstruction of gas-liquid (green) and oil water (red) interfaces from the contour plots of a gas volume fraction of 0.8 and an oil volume fraction of 0.5.

Figure 9A:
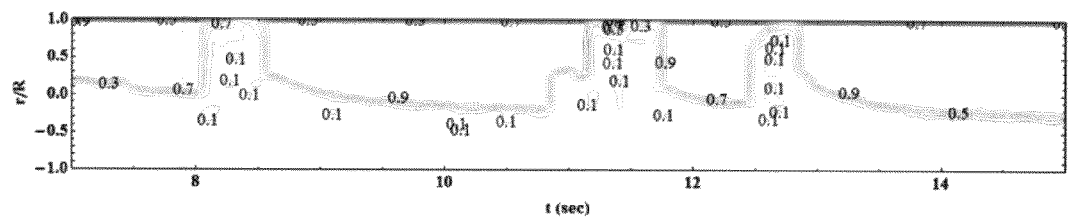
Figure 9B:
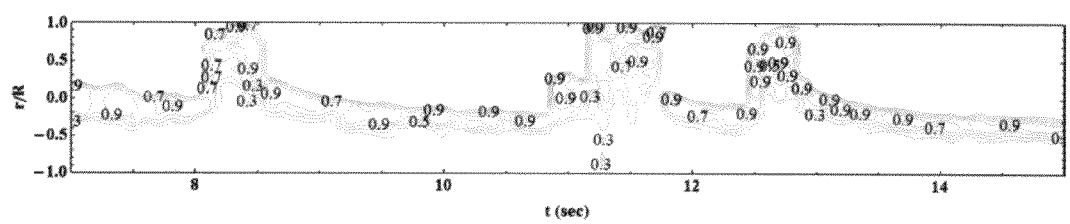
Figure 9C:
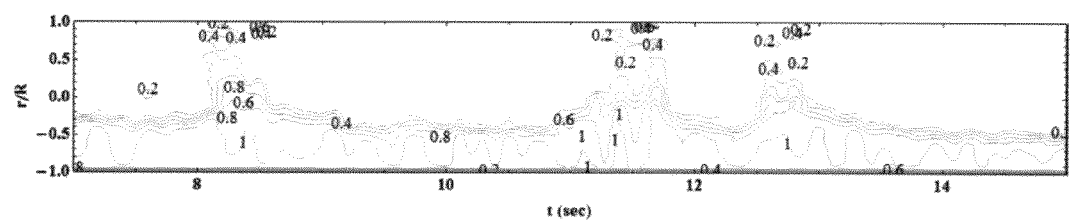

FIG. 9a is a contour plot for gas on a vertical slice intersecting through the pipe centre along the pipe. FIG. 9b shows contour plot for oil, and FIG. 9c for water.

FIG. 10a shows X-ray, soft or hard, passing vertically through left, middle and right column or pipe section (in the middle). The same radiation intensity is measured at the sensor for the three situations: in the left column which is imagined, gas (upper, green) and oil (lower, red); in the middle (pipe section), which may be considered real, the upper, green is gas, the middle, red is oil, and the lower, blue is water; and in the right column, which again is imagined, upper, green is gas, lower, blue is water. A sensor is arranged below each column and the pipe.

FIG. 10b shows, corresponding to FIG. 10a, imagined oil and water in the left column, gas, oil and water in the middle, which is the pipe section, and imagined gas and water in the right column.

FIG. 11a shows results of using the prior art method of direct conversion of gas volume fraction, between the top and bottom of a gas-liquid mixture. The abscissa is in seconds from 0 to 30 s.

FIG. 11b illustrates calculated values of gas volume fraction calculated according to the present invention, between the top and bottom of a gas-liquid mixture.

Figure 12A:
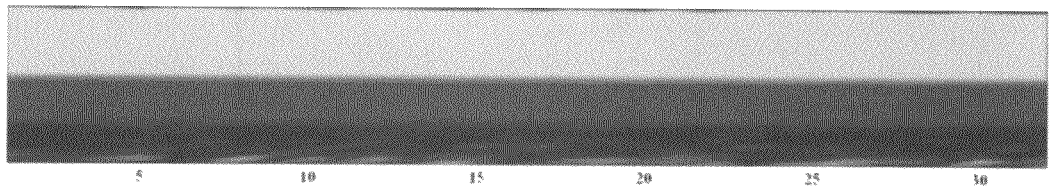
Figure 12B:
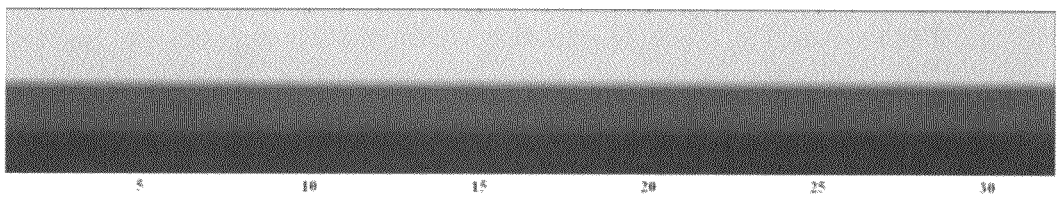

FIG. 12a shows a tomographic time sequence of a passing three-phase flow of gas (upper), oil (middle) and water (lower) calculated using direct conversion of the prior art, and FIG. 12b shows a similar tomographic time sequence calculated according to the present invention.

Figure 13A:
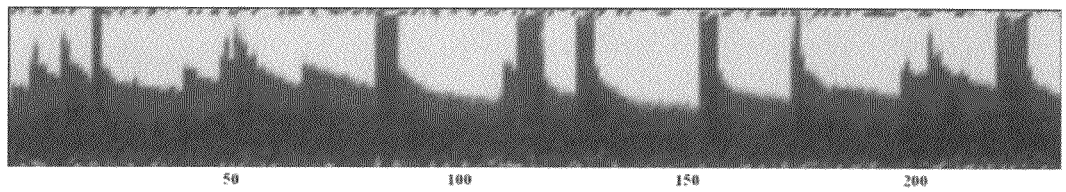
Figure 13B:
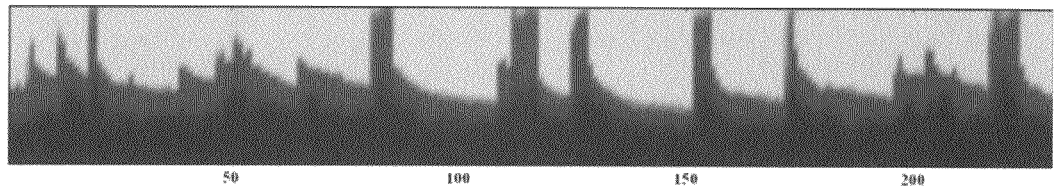

FIG. 13a shows a tomographic time sequence calculated according to the direct conversion method, of a passing three-phase flow of gas, oil and water as for FIG. 12a, but wherein there are slugs of oil and water passing at irregular intervals. The abscissa is in seconds from 0 to about 225 s. FIG. 13b shows tomographic images calculated on the basis of the same measurements but using the method of the present invention.

Figure 14:
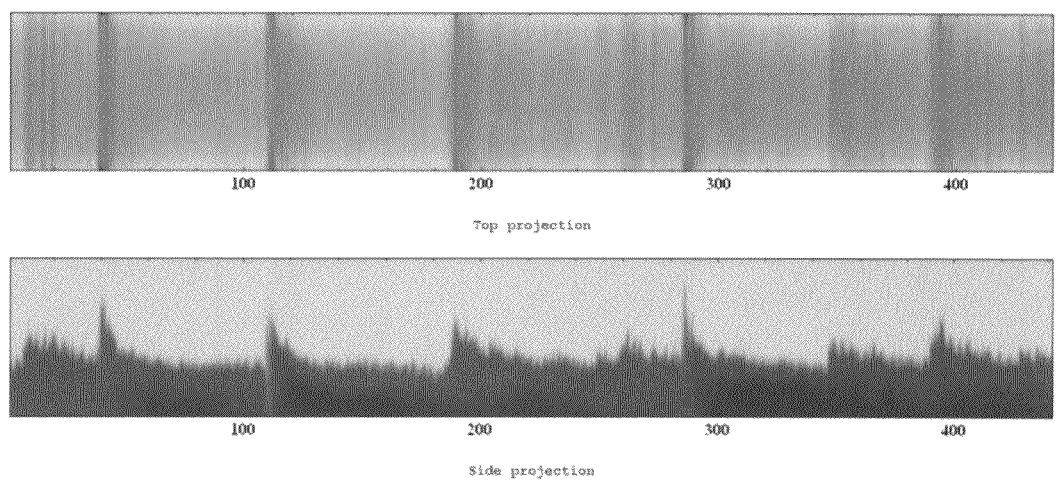

FIG. 14 shows vertical and horizontal projection images of a passing flow calculated according to the present invention.

BRIEF SUMMARY OF THE INVENTION

The invention provides improved calculations of chordal holdup values of three-phase flow through a volume. In an embodiment of the invention it provides better estimates of the chordal holdup values due to utilizing less error-prone lower and upper bounds to the gas and water holdups calculated from an imagined two-phase fluid content in the volume. The invention is a method of estimating chordal holdup values of gas, oil and water ($\epsilon_G$, $\epsilon_O$, $\epsilon_W$) for tomographic imaging of a three-phase flow through a volume, comprising the steps of:
  providing one or more X-ray sources arranged for irradiating through said volume and two or more X-ray sensors arranged for discriminating at least partly between a first and a second or more radiation bands,
  irradiating said volume and conducting first and second calibration measurements ($I_G^S$, $I_O^S$, $I_W^S$), ($I_G^H$, $I_O^H$, $I_W^H$) of said first and said second radiation bands of said X-ray sensors for gas only, oil only, and water only present in said volume, respectively,
  arranging a mixture of two or more fluids of gas, oil and water in said volume, and
  irradiating said volume and conducting X-ray measurements ($I^S$, $I^H$) in said first and second radiation bands,
  while using an established relationship between a function of holdup values $f(\epsilon_G, \epsilon_W)$ of at least gas and water and said X-ray measurements ($I^S$, $I^H$) on said mixture in said first and second radiation bands, searching holdup values $\epsilon_G$, $\epsilon_W$ that minimize said function of holdup values $f(\epsilon_G, \epsilon_W)$ under the constraints of the sum of said holdup values of gas and water being more than or equal to zero and less than or equal to one, i.e. that $0 \leq \epsilon_G + \epsilon_W \leq 1$.

In an advantageous embodiment of the invention the method comprises searching said holdup values ($\epsilon_G$, $\epsilon_W$) under further constraints than above. The further constraints are as follows:
  first, said holdup value of gas $\epsilon_G = \epsilon_G^{GOW}$ as calculated considering presence of oil and water is larger than or equal to a holdup value of gas $\epsilon_G^{GO}$ calculated considering presence of oil only, and less than or equal to a holdup value of gas $\epsilon_G^{GW}$ calculated considering presence of water only, i.e. $\epsilon_G^{GO} \leq \epsilon_G^{GOW} \leq \epsilon_G^{GW}$.
  Said holdup value of gas $\epsilon_G^{GOW}$ is equal to or more than zero and less than or equal to one, i.e. $0 \leq \epsilon_G^{GOW} \leq 1$.
  secondly, said holdup value of water $\epsilon_W = \epsilon_W^{GOW}$ calculated considering both the presence of gas and oil is larger than a holdup value of water $\epsilon_W^{WO}$ calculated considering presence of oil only, and less than a holdup value of water $\epsilon_W^{WG}$ calculated considering presence of gas only, i.e. $\epsilon_W^{WO} \leq \epsilon_W^{GOW} \leq \epsilon_W^{WG}$. As for gas, said holdup value of water $\epsilon_W^{GOW}$ is larger than or equal to zero and less than or equal to one, i.e. $0 \leq \epsilon_W^{GOW} \leq 1$.

Further embodiments of the invention are given in the dependent claims.

Embodiments of the Invention

Figure 1:
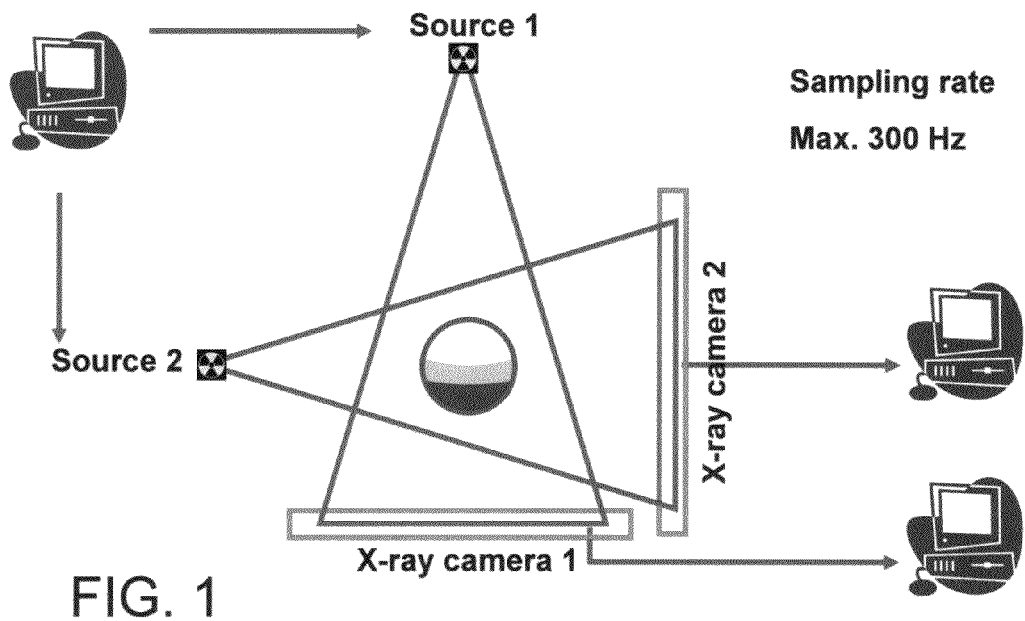
Figure 2A:
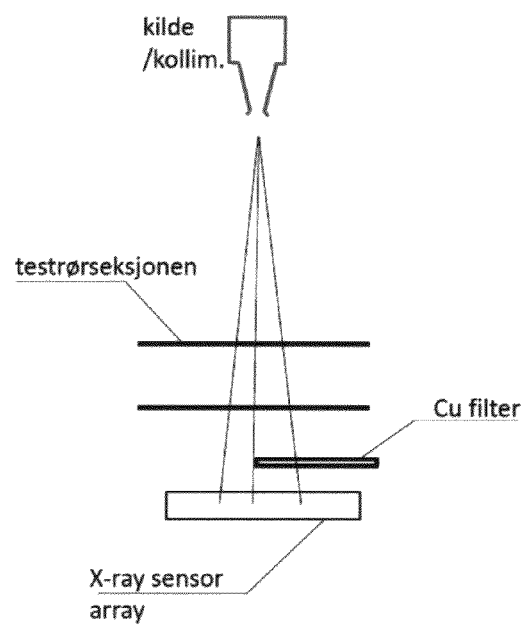
Figure 2B:
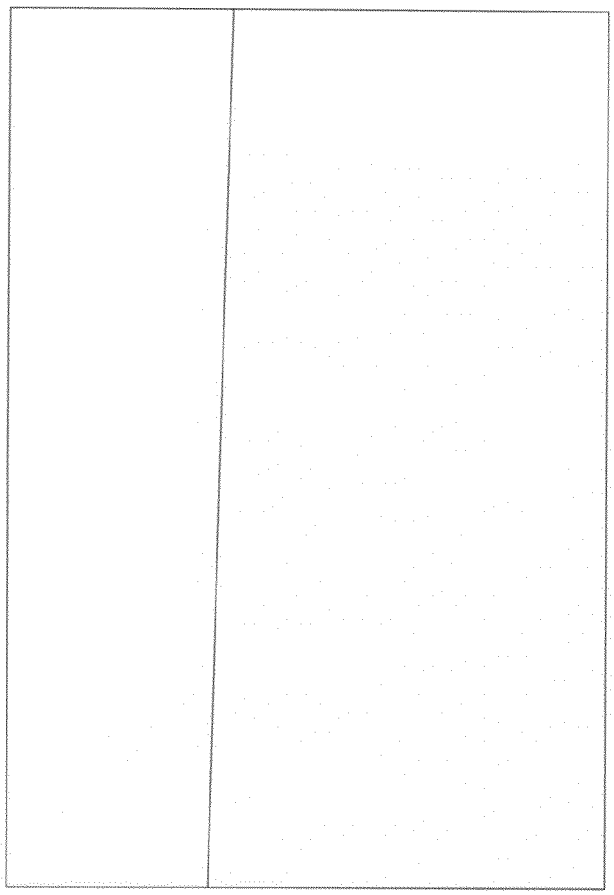
Figure 3A:
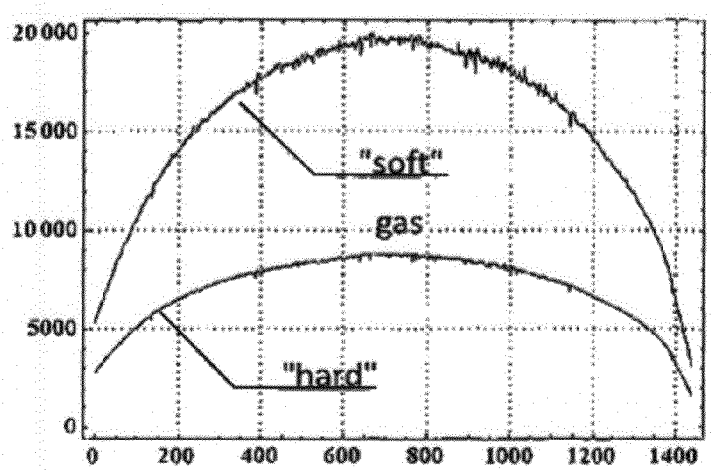
Figure 3B:
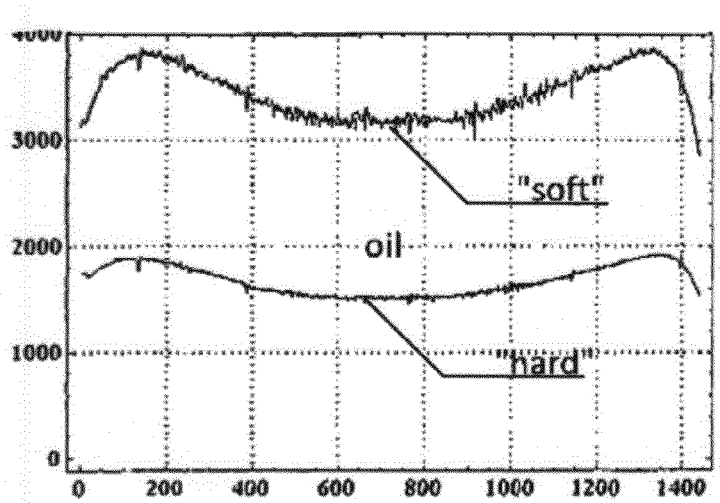
Figure 3C:
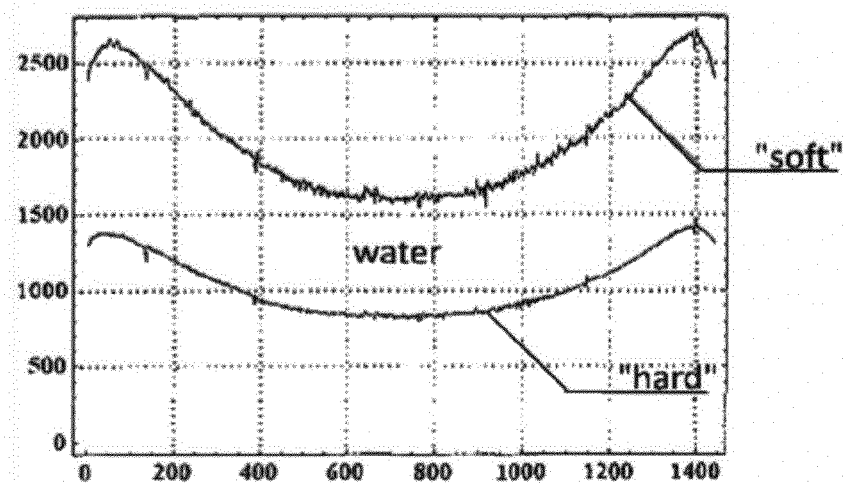

Following the use of the copper filter and above setup, the operation of the system mainly becomes the use of calibration data together with measurements of the filtered and unfiltered signal. FIGS. 3(a)-3(c) show the examples of the calibration curves for soft and hard beams (lower curve); the vertical axis corresponds to the grey level. About 1500 pixels in the transverse direction lie in the effective shadow area. The invention is a method of estimating chordal holdup values of gas, oil and water ($\epsilon_G$, $\epsilon_O$, $\epsilon_W$) for tomographic imaging of a three-phase flow through a volume. The method comprises the following steps:
  One or more X-ray sources is provided, arranged for irradiating through the volume and two or more X-ray sensors are arranged for discriminating at least partly between a first and a second radiation band.
  The volume is radiated and first and second calibration measurements ($I_G^S$, $I_O^S$, $I_W^S$), ($I_G^H$, $I_O^H$, $I_W^H$) are conducted of the first and the second radiation bands of the X-ray sensors for gas only, oil only, and water only present in the volume, respectively. Such calibration measurements are illustrated in FIGS. 3a, b, and c.
  A mixture of two or more fluids of gas, oil and water are arranged in the volume and irradiated, X-ray measurements ($I^S$, $I^H$) of the fluid flow in the first and second radiation bands are conducted.
  The holdup values of are then calculated. While using an established relationship between a function of holdup values $f(\epsilon_G, \epsilon_W)$ of at least gas and water and said X-ray measurements ($I^S$, $I^H$) on said mixture in said first and second radiation bands, one searches for holdup values $\epsilon_G$, $\epsilon_W$ that minimize the function of holdup values $f(\epsilon_G, \epsilon_W)$ under the constraints of the sum of the holdup values of gas and water being more than or equal to zero and less than or equal to one, i.e. that $0 \leq \epsilon_G + \epsilon_W \leq 1$.

In an embodiment of the invention the relationship between a function of holdup values $f(\epsilon_G, \epsilon_W)$ of at least gas and water and said X-ray measurements on said mixture in said first and second radiation bands is:

$$f(\varepsilon_G, \varepsilon_W) = \left[1 - \left(\frac{I^S}{I_G^S}\right)^{\varepsilon_G} \left(\frac{I^S}{I_O^S}\right)^{1-\varepsilon_G-\varepsilon_W} \left(\frac{I_S}{I_W^S}\right)^{\varepsilon_W}\right]^2 + \left[1 - \left(\frac{I^H}{I_G^H}\right)^{\varepsilon_G} \left(\frac{I^H}{I_O^H}\right)^{1-\varepsilon_G-\varepsilon_W} \left(\frac{I^H}{I_W^H}\right)^{\varepsilon_W}\right]^2.$$

In an advantageous embodiment of the invention the method comprises searching the holdup values ($\epsilon_G$, $\epsilon_W$) under further constraints than above. The further constraints are as follows:
  first, said holdup value of gas $\epsilon_G = \epsilon_G^{GOW}$ as calculated considering presence of oil and water is larger than or equal to a holdup value of gas $\epsilon_G^{GO}$ calculated considering presence of oil only, and less than or equal to a holdup value of gas $\epsilon_G^{GW}$ calculated considering presence of water only, i.e. $\epsilon_G^{GO} \leq \epsilon_G^{GOW} \leq \epsilon_G^{GW}$.

Said holdup value of gas $\epsilon_G^{GOW}$ is equal to or more than zero and less than or equal to one, i.e. $0 \leq \epsilon_G^{GOW} \leq 1$.

secondly, said holdup value of water $\epsilon_W = \epsilon_W^{GOW}$ calculated considering both the presence of gas and oil is larger than a holdup value of water $\epsilon_W^{WO}$ calculated considering presence of oil only, and less than a holdup value of water $\epsilon_{WG}$ calculated considering presence of gas only, i.e. $\epsilon_W^{WO} \leq \epsilon_W^{GOW} \leq \epsilon_W^{WG}$. As for gas, said holdup value of water $\epsilon_W^{GOW}$ is larger than or equal to zero and less than or equal to one, i.e. $0 \leq \epsilon_W^{GOW} \leq 1$.

The above use of constraints may be explained as follows: Imagine X-ray, soft or hard, passing vertically through left, middle and right column of FIG. 10a. The same radiation intensity is measured at the sensor for the three situations: in the left column, gas (upper, green) and oil (lower, red); in the middle (pipe section) the upper, green is gas, the middle, red is oil, and the lower, blue is water; and in the right column upper, green is gas, lower, blue is water. A sensor is arranged below each column and the pipe section in the middle. $\epsilon_G^{GOW}$ is shown in the middle "column" (section) as an intermediate between the gas holdup to the left and to the right. The gas holdup $\epsilon_G^{GO}$ based on O/G is a lower bound, please see the left two-phase column, because the attenuating density of oil is less than for water (less than for oil and water) so less gas will apparently be present for the same measured radiation intensity at the sensor.

Further, the gas holdup $\epsilon_G^{GW}$ based on W/G is an upper bound for the gas holdup in three-phase, please see right two-phase column of FIG. 10a, because the attenuating density of water is higher than for oil (higher than for oil and water) so more gas will apparently be present for the same measured radiation intensity at the sensor.

Conversely, please see FIG. 10b, a holdup value of water $\epsilon_W^{GOW}$ is calculated considering presence of gas and oil is larger than a holdup value of water $\epsilon_W^{WO}$ calculated considering presence of oil only, please see left column of FIG. 10b which is a lower bound, and less than a holdup value of water $\epsilon_W^{WG}$ calculated considering presence of gas only, which is an upper bound, again because gas attenuates radiation less than oil, and the radiation imagined under two-phase operation at the sensors are equal.

If assuming constant attenuation coefficients for gas, oil and water phases, in each energy band, for given X-ray operation conditions, one can derive the following formulae to compute the chordal holdups of phases.

$$\varepsilon_G = \left[ \frac{\log(I^S/I_O^S)}{\log(I_W^S/I_O^S)} - \frac{\log(I^H/I_O^H)}{\log(I_W^H/I_O^H)} \right] / \left[ \frac{\log(I_G^S/I_O^S)}{\log(I_W^S/I_O^S)} - \frac{\log(I_G^H/I_O^H)}{\log(I_W^H/I_O^H)} \right] \quad (1)$$

$$\varepsilon_W = \left[ \frac{\log(I^S/I_G^S)}{\log(I_O^S/I_G^S)} - \frac{\log(I^H/I_G^H)}{\log(I_O^H/I_G^H)} \right] / \left[ \frac{\log(I_W^S/I_G^S)}{\log(I_O^S/I_G^S)} - \frac{\log(I_W^H/I_G^H)}{\log(I_O^H/I_G^H)} \right] \quad (2)$$

$$\varepsilon_O = 1 - \varepsilon_G - \varepsilon_W \quad (3)$$

where $\epsilon_G$, $\epsilon_O$ and $\epsilon_W$ are the volume fraction of gas, oil and water. I is the measured data with subscripts G, O and W for gas, oil and water calibration respectively, and superscripts S and H for measured values from soft and hard beams, respectively. The above equations can then be used for all the beams from the two cameras to get the chordal holdup values, which can then be easily integrated to get the total holdup in the pipe cross-section.

FIG. 11a shows results of using the prior art method of direct conversion of gas volume fraction.

Using Equations (1-3), phase holdups can be determined directly based on measured and calibrated values. In general, this is the approach which has been broadly used today for analyzing data from dual energy gamma densitometers and X-ray tomography (see Odozi, 2000; Hu et al., 2005). However, the attenuation coefficients are not constant values in reality, varying with the radiation energy. Error analysis of the above equations (1 to 3) indicates that the computed holdups can be significantly affected by a small error in the measured data. As also found in this study, the direct application of the above expressions can sometimes lead to large errors in the results, occasionally unreasonable negative holdups being given.

To overcome this hurdle, in this study we have developed the new method, and in an embodiment of the method, an algorithm. After revisiting Equations (1-3) with some rearrangements, we can describe the solution as searching the corresponding holdups that minimize a function $f(\epsilon_G, \epsilon_W)$ as follows:

$$f(\varepsilon_G, \varepsilon_W) = \left[ 1 - \left(\frac{I^S}{I_G^S}\right)^{\varepsilon_G} \left(\frac{I^S}{I_O^S}\right)^{1-\varepsilon_G-\varepsilon_W} \left(\frac{I^S}{I_W^S}\right)^{\varepsilon_W} \right]^2 + \left[ 1 - \left(\frac{I^H}{I_G^H}\right)^{\varepsilon_G} \left(\frac{I^H}{I_O^H}\right)^{1-\varepsilon_G-\varepsilon_W} \left(\frac{I^H}{I_W^H}\right)^{\varepsilon_W} \right]^2 \quad (4)$$

As explained above, in view of physical constraints, one can deduce that the chordal volume fraction of gas phase in three-phase measurements should not exceed the range obtained in the 'assumed' corresponding two-phase system. Namely, the gas holdup in the presence of oil and water phases should be higher than the computed value by assuming only oil is the liquid phase, and lower than the holdup value estimated from assuming that only water is the liquid phase in the gas-water two-phase expression, please see Eq. (5). Similar deduction as made above can be derived for water holdup in that water holdup in three-phase system should be larger than that computed from oil-water two-phase expression and lower than that from gas-water two-phase expression (see Equations 6-7). In addition, the holdup values should always be in the range of 0-1.

FIG. 11b illustrates calculated values of gas volume fraction calculated according to the present invention, between the top and bottom of a gas-liquid mixture, and it is clear that the results are far better constrained near 1 for the measurements above the liquid surface, and that all gas volume fractions calculated below the gas/liquid interface are near zero or zero. We also immediately see that obvious errors in FIG. 11a appear when the gas holdup value is more than one, or less than zero, which is not possible.

Similarly, FIG. 12a shows a tomographic time sequence of a passing three-phase flow of gas (upper), oil (middle) and water (lower) calculated using direct conversion of the prior art, and FIG. 12b shows a similar tomographic time sequence based on the same data but calculated according to the present invention's algorithm. The general horizontal layering appear clearly from both images, but it appears clearly that less probable structures in FIG. 12a such as pockets of gas and oil in the water layer, or pockets of oil in the gas layer, are significantly reduced in FIG. 12b calculated according to the present invention.

Please notice that lower and upper bounds for gas, and lower and upper bounds for water are found using the considerations above, because the density of gas is lowest of the three-phase mixture, and because the density of water is the highest of the components of the three-phase mixture.

The problem then becomes a constrained minimization problem, i.e. minimizing Equation (4) with the constraints of Equations (5-7):

$$\epsilon_G^{GO} \leq \epsilon_G \leq \epsilon_G^{GW} \text{ and } 0 \leq \epsilon_G \leq 1 \quad (5)$$

$$\epsilon_W^{WO} \leq \epsilon_W \leq \epsilon_W^{WG} \text{ and } 0 \leq \epsilon_W \leq 1 \quad (6)$$

$$0 \leq \epsilon_G + \epsilon_W \leq 1 \quad (7)$$

For the imagined two-component bounds with gas and oil only, and gas and water only, respectively, please ref. FIG. 10a, $$\varepsilon_G^{GO} = \frac{\log(I^S/I_O^S)}{\log(I_G^S/I_O^S)} \quad (8)$$

and $$\varepsilon_G^{GW} = \frac{\log(I^S/I_W^S)}{\log(I_G^S/I_W^S)}$$

and for the imagined two-component bounds with water and oil, and gas and water, respectively, please ref. FIG. 10a, $$\varepsilon_W^{WO} = \frac{\log(I^S/I_O^S)}{\log(I_W^S/I_O^S)} \quad (9)$$

and $$\varepsilon_W^{WG} = \frac{\log(I^S/I_G^S)}{\log(I_W^S/I_G^S)}$$

Please see FIG. 3(a)-3(c) for single phase calibration curves for gas (a), oil (b) and water (c), wherein the lower curves are from hard beams and the upper curves are for soft beams.

To state the method of the invention using the constraints in other words, first, we process the data as if they came from three different two phase systems: gas and oil, gas and water, and oil and water. This gives the constraints, $\epsilon_G^{GO} \leq \epsilon_G^{GOW} \leq \epsilon_G^{GW}$, and $0 \leq \epsilon_G^{GOW} \leq 1$, and $\epsilon_W^{WO} \leq \epsilon_W^{GOW} \leq \epsilon_W^{WG}$, and $0 \leq \epsilon_W^{GOW} \leq 1$.

Then we expect that the holdup of water and gas, respectively, lie within their appropriate constraints. Then we process the data again, as for a three-phase system, subject to the constraints calculated as if the measurements were made under the three different two-phase systems.

The system can deliver three-phase measurements with a reasonably good accuracy. The absolute errors for mean holdups are found to be within ±3% for gas and ±5% for oil and water phases.

The chordal holdups values from two cameras are combined to reconstruct the tomographs, providing cross-sectional distribution of phases. The detailed analysis approaches were described in detail in the previous studies by Hu et al. (2005, 2009 and 2010).

In an embodiment of the invention, X-ray sensors arranged for single-photon counting mode may be used. Such sensors may be arranged for discriminating between two or more energy bands and counting them separately. Thus the method of the invention as described in the independent claim may include that the first radiation band of the sensors is a so-called "lower" energy band, e.g. conducted with sensors arranged for discriminating between photons of lower and higher energy, and that the second radiation band of the sensors is a so-called "high" energy band, e.g. that the measurements are conducted with sensors arranged for discriminating between photons of lower and higher energy, ref. U.S. Pat. No. 7,829,860 Nygård et al., 2010. Thus the copper filters described above are not strictly required, and as a result better energy discrimination may be achieved which may provide better estimates of the different holdups.

In an embodiment the number of said X-ray sources are two. The X-ray sources may be more than two. The X-ray sources may emit in different energy bands so as for providing different sensed energy bands. The X-ray sensors may be arranged in an array of width of between one and 560 or more X-ray pixel sensors and a length of between two and 1500 or more pixel X-ray sensors, the long direction of the array arranged transversely on the flow direction of fluids. The first and the second or more radiation bands are discriminated by use of one or more filters over part of said sensors. The first and second or more radiation bands may be discriminated by use of energy-discriminating pixel sensors. Any combination of the above embodiments of X-ray sources, the number of X-ray sources, type of discriminating sensors may be employed.

Results and Discussion

The focus of the present invention is the development of the three-phase X-ray tomography system and its potential application in multiphase pipeline researches. In what follows, the results from a three-phase slug flow in a 1 degree upward inclined pipe at $U_{SG}$=1.2 m/s, $U_{SO}$=0.05 m/s and $U_{SW}$=0.2 m/s are illustrated. The multifold competences of the current system in providing detailed measurements in large diameter three-phase flows are discussed.

Projections

Figure 4:
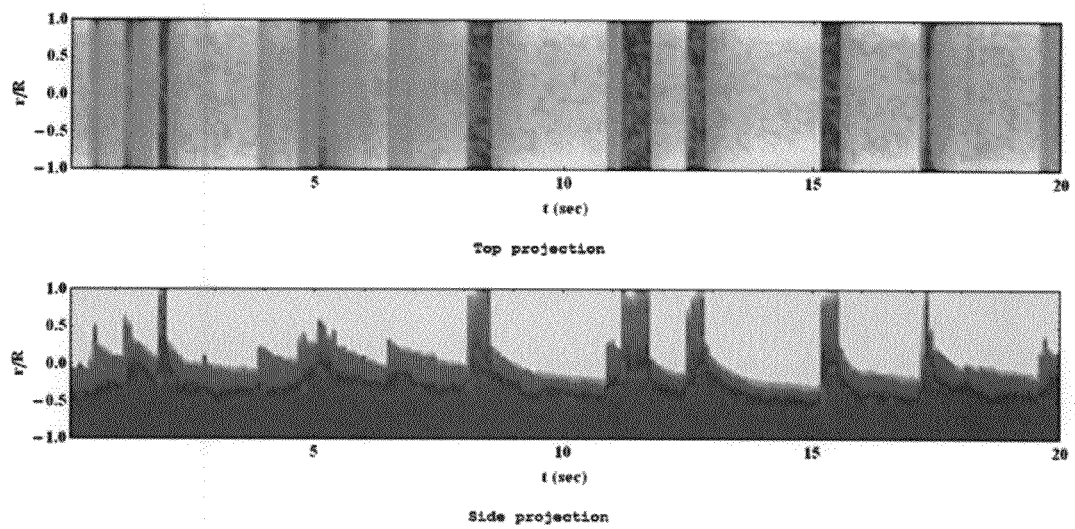
FIG. 4 shows top projection and side projection of chordal holdups of each phase, shown in green for gas, red for oil, and blue for water, which is easiest discriminated visually in the lower part of the figure. The time history plot (projection views) of three-phase slug flows are visualized by the two X-ray cameras, top view from camera 1 and side view from camera 2.

The projection views of the flow, captured by the two X-ray cameras, can give a direct 'visualization' of the flow. FIG. 4 shows the passage of a number of slugs and waves through the measurement location. Aside from the flow pattern, the mixing, distribution and transport process of gas in the slug body can also be observed in some detail. Here, green, red and blue colours correspond to pure gas, oil and water phases, respectively. The same colour scheme is used for plotting tomographs.

Figure 5A:
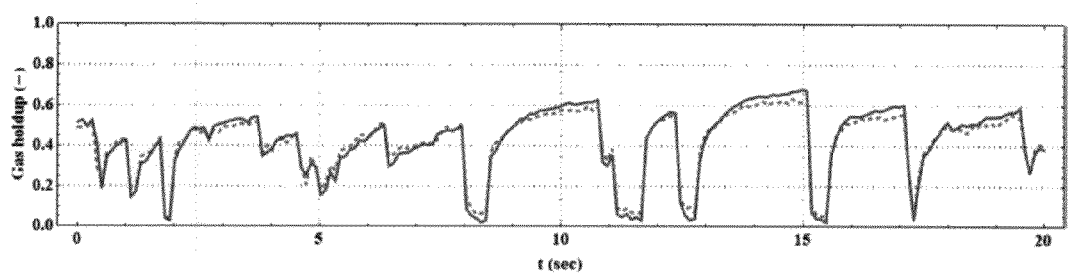
FIG. 5 shows the time traces for the average cross-sectional holdups of respective phase. The measured holdup values from Camera 1 are plotted in solid lines and those from Camera 2 in dashed lines.
Figure 5B:
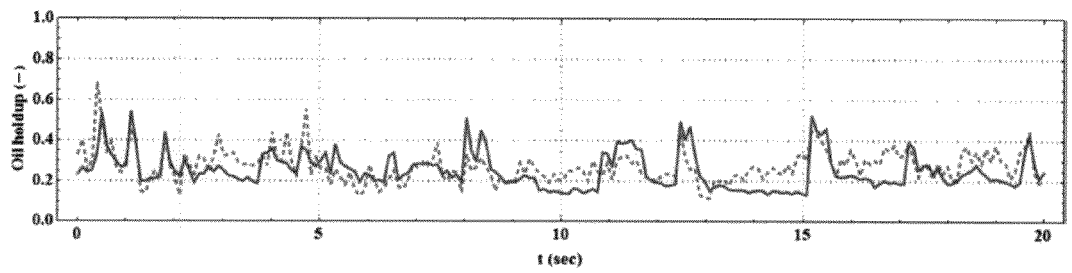
Figure 5C:
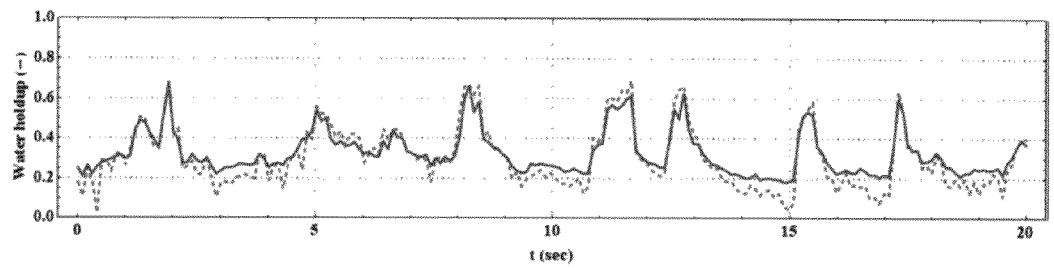

By integrating the chordal holdups of each phase from FIG. 4, one can also obtain the time traces for the average cross-sectional holdups of respective phase which is given in FIG. 5. The measured holdup values from Camera 1 are plotted as solid lines and those from Camera 2 as dashed lines. As shown, the results from two cameras are fairly consistent. Since the measurements by the two cameras are independent, the consistency implies the success of the present instrument in three-phase experiments. In contrast to the time traces typically measured by gamma densitometer, the X-ray system can give much more insights in the flow structure and phase distribution even by direct 'visualisation' of the flows from two directions. For example, the difference between slug and large wave, whose holdup traces could be rather similar, can be easily distinguished by the projection views. This will enable very accurate analysis of slug or wave characteristics.

Tomographs

Figure 6:
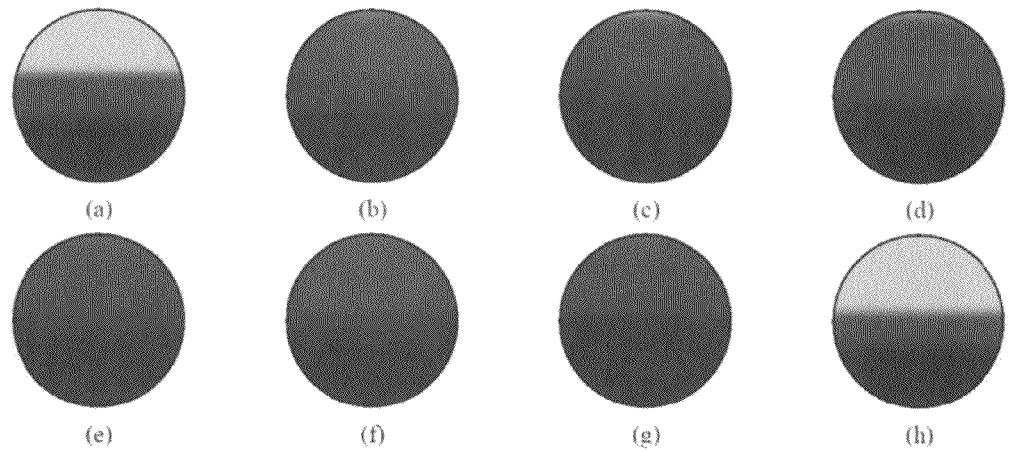

Having acquired the chordal holdups, we can also reconstruct the tomographs using the algorithm developed previously by Hu et al. (2005). FIG. 6 shows a sequence of tomographs for the passage of a three-phase slug, observed at 8 seconds in FIG. 4. FIGS. 6a and 6h refer to the stratified regions ahead and after the slug, respectively. According to FIGS. 6b-6g for the slug body, we see that the mixing of phases is predominantly happening on the upper part of the pipe. Due to the low slug velocity reported here, no severe mixing of oil-water has been observed and instead, oil and water are seen to be separated fairly quickly (see FIG. 6h).

Reconstruction of Three-Dimensional Interfaces

By combining a sequence of tomographs at different time (e.g. FIGS. 6a to 6h), we can also reconstruct the 3D flow, a pseudo steady structure as seen by the X-ray CT. An example is illustrated in FIG. 7 of reconstructed gas-liquid interface from the 3D contour plot of the gas volume fraction of 0.8; a maximum droplet fraction of 0.2 is assumed at the gas-liquid boundary. In FIG. 7, three slugs captured between 7-15 seconds are shown. Analogously, the oil-water interface is also plotted from the contour plot of oil holdup of 0.5; oil-water boundary is assumed at oil holdup of 0.5 (this is just a rough estimate based on the possible phase inversion point). The structure of oil-water interface in comparison with gas-liquid interface is illustrated in FIG. 8.

Slice View

Once the flow has been reconstructed in three dimensions, one can obtain information for any slice through the flow. FIG. 9 illustrates three contour plots of gas, oil and water phases on the vertical slice through the pipe centre. Note that FIG. 9 shows the distributions of the phases in a space-time plane; flow is evolving as measurements are conducted. Thus this is not a longitudinal image of the entire pipe at one instant. However, the results are still very useful in studying the mixing of the phases and their distributions.

FIG. 13a shows a tomographic time sequence calculated according to the direct conversion method, of a passing three-phase flow of gas, oil and water as for FIG. 12a, but wherein there are slugs of oil and water passing at irregular intervals. The abscissa is in seconds from o to about 225 s. FIG. 13b shows tomographic images calculated on the basis of the same measurements but using the method of the present invention. Prominent features in the calculated images of FIG. 13a are the apparent oil at the ceiling wall of the pipe, and apparent oil at the bottom wall of the pipe, while those features are absent from the ceiling and bottom wall of the pipe as calculated using the present invention. Thus we may conclude that according to tomographic images calculated according to the present invention, there is no significant amount of oil along the upper wall of the pipe, nor any significant amount of oil along the bottom wall of the pipe. Further, there is a clearer distinction with less mixing of oil and water in the lower water zone as calculated with the present invention, while there still seems to be some water in the oil, although less than what is calculated using the direct conversion method of the prior art. All in all, the image calculated according to the invention seems to indicate a far better separated flow despite the presence of slugs, but the overall slug picture remains.

FIG. 14 shows vertical and horizontal projection images of a passing flow calculated according to the present invention. It will be realized that the highest oil peaks seen clearly in the horizontal projections are clearly present in the entire width of the pipe as seen in the vertical projection, too, so they are consistent.

The detail of the tomographic images provides an opportunity to better understand the three-phase flow, and also a better basis for fiscal calculations.

The present invention calculates three-phase holdup values using constraints from corresponding calculations on imagined two-phase flows, thus providing upper and lower bounds for the lightest and densest components gas and water. The present method may be extended to calculate more than three phases hold-up, for example gas, oil, water and sand particles contents in a flow of four phases of different densities, and using bounds calculated from imagined flows of fewer phases, as a development from the present invention, but the related similar bounds and constraints are only two, are obtained for the lightest and the heaviest phase.

The present invention is presented for gas, oil and water, but would work well with gas, oil and sand. It would also work fine for oil, water and sand.

With the method of the invention one is able to achieve a noise reduction by a factor 5 to 20 or more, please see FIG. 11a compared with FIG. 11b which demonstrates a significant noise reduction between the gas holdup values calculated using prior art and the method of the invention. This applies to the chordal holdup measurement determined using the algorithm on actual measurements. Absolute errors for mean holdups are found to be within +/−3% for gas and +/−5% for oil and water phases. The definition of absolute error for holdup is simply |HM−HT|, where HM is measured holdup, HT is true holdup, both in %. True holdup can be known in some cases. For example: holdup may be measured directly on a static system of liquids and gas; we sometimes make test measurements on solid "dummies" which are made to precise dimensions.

Following previous work, a fast response three-phase X-ray tomography system has been successfully developed and tested in a large diameter high pressure multiphase pipeline at IFE, Norway. The development of the present X-ray system and its potential application in multiphase flow research, as illustrated, have provided us with a valuable tool to capture the details and gain better insight into complex three-phase flow behaviour. The quantitative information obtained from this instrument can be very helpful in validating the closures used in CFD simulations and 1D models. Of particular importance in most oil industries is the understanding of internal flow structures in flows with opaque fluids, such as transport of crude/heavy oil, for which conventional techniques are useless. Such problems are eliminated when an X-ray CT system, a non-intrusive instrument, is employed.

REFERENCES

Acikgoz, M., Lahey, Jr., R. T. and França, F. (1992). An experimental study of three-phase flow regimes, Int. J. Multiphase Flow, Vol. 18, No. 3, p. 341.

Hall, A. R. W. (1992). Multiphase flow of oil-water-gas in Horizontal pipes, Ph.D. dissertation, University of London.

Hu, B., Stewart, C., Hale, C. P., Lawrence, C. J., Hall, A. R. W., Zwiens, H., Hewitt, G. F. (2005). Development of an X-ray computed tomography (CT) system with sparse sources: application to three-phase pipe flow visualization, Exp. in Fluids, 39, 667-678.

Hu, B., Langsholt, M., Nuland, S., Lawrence, C. J. (2009). Void distribution in the liquid layer in stratified wavy flows measured with an X-ray Computed Tomography instrument, 14th BHR Conference, Cannes, France.

Hu, B., Nuland, S., Nossen, J., Langsholt, M., Lawrence, C. J. (2010). Entrainment of gas into slugs and its subsequent transport in two-phase slug flow, 7th North American Conference on Multiphase Technology, Banff, Canada, 2-4 Jun. 2010.

Langsholt, M., Pettersen, B., Andersson, P. (2002). Pipe inclination effects on three-phase slug flow characteristics, IFE internal report IFE/KF/R/2001-064, Institute for Energy Technology, Norway.

Odozi U. A., (2000). Three-phase gas-liquid-liquid slug flow, Ph.D thesis, University of London.

Pan, L. (1996). High pressure three-phase (gas/liquid/liquid flow), Ph.D. thesis Imperial College, University of London.

Sobocinski, D. P. (1955). Horizontal concurrent flow of air, gas-oil, and water in a horizontal pipe, M. S. Thesis University of Oklahoma.

Valle, A. (2000). Three phase gas-oil-water pipe flow, Ph.D. thesis, University of London.

Wilkens, R. J. (1997). Prediction of the flow regime transitions in high pressure, large diameter inclined multiphase pipelines. Ph.D. Dissertation, Ohio University, OH.

We claim:

1. A method of estimating chordal holdup values of gas, oil and water ($\epsilon_G$, $\epsilon_O$, $\epsilon_W$) for tomographic imaging of a three-phase flow through a volume, comprising:
   providing one or more X-ray sources arranged for irradiating through said volume and two or more X-ray sensors arranged for discriminating at least partly between a first and a second or more radiation bands,
   conducting first calibration measurements ($I_G^S$, $I_O^S$, $I_W^S$) of said first radiation band of the X-ray sensors for only gas, only oil, and only water present in said volume, respectively,
   conducting second calibration measurements ($I_G^H$, $I_O^H$, $I_W^H$) of said second radiation band of the X-ray sensors for only gas, only oil, and only water present in said volume, respectively,
   arranging a mixture of two or more fluids of gas, oil and water in said volume,
   irradiating said volume and conducting X-ray measurements ($I^S$, $I^H$) in said first and second radiation bands,
   establishing a relationship between a function of holdup values $f(\epsilon_G, \epsilon_W)$ of at least gas and water and said X-ray measurements ($I^S$, $I^H$) on said mixture in said first and second radiation bands,
   searching holdup values $\epsilon_G$, $\epsilon_W$ that minimize said function of holdup values $f(\epsilon_G, \epsilon_W)$ under the constraints of the sum of said holdup values of gas and water is more than or equal to zero and less than or equal to one, i.e. that $0 \leq \epsilon_G + \epsilon_W \leq 1$.

2. The method of claim 1, searching said holdup values ($\epsilon_G$, $\epsilon_W$) under the further constraints of
   said holdup value of gas $\epsilon_G = \epsilon_G^{GOW}$ calculated considering presence of oil and water is larger than or equal to a holdup value of gas $\epsilon_G^{GO}$ calculated considering presence of oil only, and less than or equal to a holdup value of gas $\epsilon_G^{GW}$ calculated considering presence of water only, and said holdup value of gas $\epsilon_G^{GOW}$ equal to or more than zero and less than or equal to one, i.e. $0 \leq \epsilon_G^{GOW} \leq 1$, and
   said holdup value of water $\epsilon_W^{GOW}$ calculated considering presence of gas and oil is larger than a holdup value of water $\epsilon_W^{WO}$ calculated considering presence of oil only, and less than a holdup value of water $\epsilon_W^{WG}$ calculated considering presence of gas only, and said holdup value of water $\epsilon_W = \epsilon_W^{GOW}$ more than or equal to zero and less than or equal to one, i.e. $\epsilon_G^{GO} \leq \epsilon_G^{GOW} \leq \epsilon_G^{GW}$, and $0 \leq \epsilon_G^{GOW} \leq 1$, and $\epsilon_W^{WO} \leq \epsilon_W^{GOW} \leq \epsilon_W^{WG}$, and $0 \leq \epsilon_W^{GOW} \leq 1$.

3. The method of claim 1, wherein said relationship between a function of holdup values $f(\epsilon_G, \epsilon_W)$ of at least gas and water and said X-ray measurements on said mixture in said first and second radiation bands is $$f(\varepsilon_G, \varepsilon_W) = \left[1 - \left(\frac{I^S}{I_G^S}\right)^{\varepsilon_G} \left(\frac{I^S}{I_O^S}\right)^{1-\varepsilon_G-\varepsilon_W} \left(\frac{I^S}{I_W^S}\right)^{\varepsilon_W}\right]^2 + \left[1 - \left(\frac{I^H}{I_G^H}\right)^{\varepsilon_G} \left(\frac{I^H}{I_O^H}\right)^{1-\varepsilon_G-\varepsilon_W} \left(\frac{I^H}{I_W^H}\right)^{\varepsilon_W}\right]^2.$$

4. The method of claim 1, searching holdup values under the further constraint that the sum of holdup values of gas, oil and water equals one, i.e. $\epsilon_G + \epsilon_O + \epsilon_W = 1$.

5. The method of claim 1, wherein said first radiation band of the sensors is a "soft" energy band, e.g. without low-energy filtering.

6. The method of claim 5, wherein said second radiation band of the sensors is a "hard" energy band, e.g. with low-energy filtering.

7. The method according to claim 1, wherein two or more sets of pairs of X-ray sources with oppositely arranged X-ray sensors are arranged about said volume.

8. The method according to claim 1, said three-phase flow passing through a pipe.

9. The method according to claim 1, wherein said fluids of gas, oil and water to be calculated holdup values for are replaced by the fluids gas, oil and the solid sand.

10. The method according to claim 1, wherein said fluids of gas, oil and water to be calculated holdup values for are replaced by the fluids oil, water and the solid sand.

11. The method according to claim 1, wherein the method is extended to four different phases such as gas, oil, water, and sand, by using two-phase calculated upper and lower bounds based on the lightest and the densest components, respectively, and solving a relation of three-phase components.

12. The method of claim 1, wherein the number of said X-ray sources are two.

13. The method of claim 1, wherein said X-ray sensors are arranged in an array of width of between one and 560 or more X-ray pixel sensors and a length of between two and 1500 or more pixel X-ray sensors.

14. The method of claim 1, wherein said first and said second or more radiation bands are discriminated by use of one or more filters over part of said sensors.

15. The method of claim 1, wherein said first and said second or more radiation bands are discriminated by use of energy-discriminating pixel sensors.

* * * * *